United States Patent [19]

Minn

[11] 4,283,335

[45] Aug. 11, 1981

[54] PROCESS FOR PRODUCING DIALKYL DITHIOPHOSPHORIC ACID ESTERS

[75] Inventor: James Minn, Hattiesburg, Miss.

[73] Assignee: Boots Hercules Agrochemicals Co., Wilmington, Del.

[21] Appl. No.: 123,547

[22] Filed: Feb. 22, 1980

[51] Int. Cl.$^3$ .................... C07D 209/48; C07F 9/173; C07D 319/12
[52] U.S. Cl. ............................. 260/326 E; 260/340.6; 260/340.9 R; 260/979; 549/14; 549/21
[58] Field of Search ................ 260/326 E, 979, 340.6, 260/340.9; 549/14, 21

[56] References Cited

U.S. PATENT DOCUMENTS

| | | | |
|---|---|---|---|
| 2,725,328 | 11/1955 | Diveley et al. | 260/340.6 |
| 2,815,350 | 12/1957 | Speck | 260/979 |

*Primary Examiner*—Donald G. Daus
*Assistant Examiner*—M. C. Eakin
*Attorney, Agent, or Firm*—Hazel L. Deming

[57] ABSTRACT

Disclosed is a method for improving the yield of dialkyl dithiophosphoric acid esters produced by the Lewis acid catalyzed reaction of an O,O-dialkyl dithiophosphoric acid and an organic chloride. More specifically, the method concerns the improvement wherein the reaction is carried out in the presence of from 0.1 to 1.5 moles, per mole of organic chloride, of an anhydride of a fatty acid containing 2 to 5 carbon atoms.

7 Claims, No Drawings

PROCESS FOR PRODUCING DIALKYL DITHIOPHOSPHORIC ACID ESTERS

This invention relates to an improved process for the preparation of dialkyl dithiophosphoric acid esters and more specifically relates to a method for improving the yield of dialkyl dithiophosphoric acid esters produced by the reaction of an O,O-dialkyl dithiophosphoric acid and an organic chloride.

It is known from U.S. Pat. No. 2,725,328 to Diveley and Lohr that organic dithiophosphoric acid esters having excellent insecticidal properties can be prepared by the substitution reaction of an O,O-dialkyl dithiophosphoric acid with a dichlorodioxane and from U.S. Pat. No. 2,815,350 to Speck that the rate of the reaction can be accelerated by carrying out the reaction in the presence of a catalytic amount of a chloride of zinc, iron or tin. Usually the reaction is conducted in a volatile hydrocarbon solvent which is inert in the reaction at temperatures up to about 110° C. using a stoichiometric excess of one of the reactants to force the reaction to completion and preferably an excess of the dialkyl dithiophosphoric acid reactant to maximize substitution and optimize yields.

Ordinarily, the dialkyl dithiophosphoric acid reactant is produced by reacting a stoichiometric excess of the alcohol, which is to form the ester part of the reactant, with phosphorus pentasulfide, preferably in a non-reactive solvent, and removing the hydrogen sulfide which is liberated. Generally, the product of the reaction is from about 85 to 90% pure, the main impurities being excess alcohol, water and neutral phosphorus compounds. Since these impurities are likewise reactive with organic chlorides, it is generally necessary to purify the ordinarily available dialkyl dithiophosphoric acid before use in order to maximize yield. Conventional purification techniques such as vacuum distillation or solvent extraction of the salt of the acid are satisfactory methods for removing the bulk of the impurities. However, purification adds considerable costs in terms of equipment and time to the over all operation and is economically unattractive, particularly for industrial scale operations.

Now in accordance with the present invention it has been found that not only is it unnecessary to remove impurities from conventionally prepared O,O-dialkyl dithiophosphoric acid before use in the substitution reaction with organic chlorides to obtain high yields of O,O-dialkyl dithiophosphoric acid esters, but that the purity of the ester product can also be improved by conducting the reaction in the presence of specified amounts of certain carboxylic acid anhydrides.

Accordingly, the invention relates to an improved process for producing O,O-dialkyl dithiophosphoric acid esters by the reaction of an O,O-dialkyl dithiophosphoric acid with an organic chloride in the presence of a catalytic amount of zinc chloride, ferrous chloride or stannous chloride, the improvement comprising effecting the reaction in the presence of from 0.1 to 1.5 moles, per mole of organic chloride, of an anhydride of a fatty acid containing 2 to 5 carbon atoms.

The process of this invention is more particularly set forth in the following examples.

EXAMPLE 1

A vessel equipped with heating means, agitator, thermometer, addition port and condenser was charged with a 60% cyclohexane solution of technical O,O-diethyl dithiophosphoric acid containing 0.3 mole of pure acid and 0.051 mole of ethanol, 0.0022 gram atom of zinc dust and 0.057 mole of acetic anhydride. Heating and agitation were commenced and the charge was heated at 80° C. for 0.5 hour, following which time 0.13 mole of 2,3-dichloro-p-dioxane was added gradually over a 1 hour period. The reaction mixture was agitated at 85° C. for an additional 3 hour period, after which the mixture was cooled to 25° C. The cooled mixture was washed first with an acidic brine solution and then with dilute caustic, and the washed solution was distilled to remove the cyclohexane. The product (50.5 grams) contained 84.4% of bis (O,O-diethyl dithiophosphate) of p-dioxane-2,3-dithiol, as determined by high pressure liquid chromatography, indicating a yield of 71.9% based on the 2,3-dichloro-p-dioxane.

When the above procedure was repeated except that no acetic anhydride was added, the product (47.9 grams) contained 60.1% of bis (O,O-diethyl dithiophosphate) of p-dioxane-2,3-dithiol, indicating a yield of 48.6% based on the 2,3-dichloro-p-dioxane.

For the sake of comparison, the above procedure was also repeated except that a molar equivalent of purified O,O-diethyl-dithiophosphoric acid (98% pure) was substituted for the technical acid and no acetic anhydride was present. This comparison example gave a product containing 85% of the desired ester, indicating a yield of 73% based on the 2,3-dichloro-p-dioxane.

EXAMPLE 2

A vessel was charged with 0.165 mole of phosphorus pentasulfide and 45 grams of cyclohexane, the charge was stirred and heated to 80° C., 0.73 mole of ethanol (equivalent to a stoichiometric excess of about 10%) was added to the charge gradually over a period of about 3 hours and the resulting mixture was stirred at 80° C. for an additional 3 hour period. Next 0.0022 gram atom of zinc dust was added to the mixture, the mixture was stirred at 80° C. for 15 minutes, 0.0057 mole of acetic anhydride was added, the mixture was stirred for 15 minutes and then 0.13 mole of 2,3-dichloro-p-dioxane was added gradually over a 1 hour period. The reaction mixture was then stirred at 85° C. for 3 hours, following which time the mixture was cooled to 25° C. and the product was recovered as in Example 1. The product (52 grams) contained 85% of bis(O,O-diethyl dithiophosphate) of p-dioxane-2,3-dithiol, indicating a yield of 74.6% based on the 2,3-dichloro-p-dioxane.

When the above procedure was repeated except that no acetic anhydride was added, the product (50 grams) contained 75% of bis(O,O-diethyl dithiophosphate) of p-dioxane-2,3-dithiol, indicating a yield of 63.3% based on the 2,3-dichloro-p-dioxane.

EXAMPLE 3

A vessel was charged with 0.33 mole of phosphorus pentasulfide and 90 grams of benzene, the charge was stirred and heated to 80° C., 1.46 moles of ethanol (equivalent to a stoichiometric excess of about 10%) were added to the charge gradually over a 3 hour period and the resulting mixture was stirred at 80° C. for an additional 3 hours. Next 0.03 gram atom of zinc dust was added to the mixture, the mixture was stirred for 15 minutes, 0.034 mole of acetic anhydride was added, the mixture was stirred again for 15 minutes and then 0.55 mole of N(1,2-dichloroethyl)phthalimide was added as a 50% solution in benzene over a period of 1 hour. The reaction mixture was then stirred at 85° C. for 5 hours, following which time the mixture was cooled to 25° C. The cooled mixture was washed first with brine and then with dilute caustic and then the benzene was removed by evaporation. The product (170 grams) contained 88% of O,O-diethyl-S-(2-chloro-1-phthalimidoethyl)phosphorodithioate, indicating a yield of 69.1% based on the N(1,2-dichloroethyl)phthalimide.

When the above procedure was repeated except that no acetic anhydride was added, the product (160 grams) contained 82% of the desired ester, indicating a yield of 60.6% based on the N(1,2-dichloroethyl)phthalimide.

As stated, the invention relates to an improved process for producing O,O-dialkyl dithiophosphoric acid esters by the reaction of an O,O-dialkyl dithiophosphoric acid with an organic chloride in the presence of a catalytic amount of zinc chloride, ferrous chloride or stannous chloride, the improvement comprising effecting the reaction in the presence of from 0.1 to 1.5 moles, per mole of organic chloride, of an anhydride of a fatty acid containing 2 to 5 carbon atoms.

The process of this invention is applicable to any O,O-dialkyl dithiophosphoric acid and is particularly interesting where the alkyl groups are those having 1 to 4 carbon atoms because of the utility of the resulting products as insecticides. However, there is no criticality with respect to the present process insofar as the alkyl groups themselves are concerned and the invention is not limited with respect thereto.

All chloro- organic compounds which contain at least one chlorine which is sufficiently active to be replaced by the O,O-dialkyl dithiophosphoric acid radical can be used in the practice of this invention. Organic chloro compounds which are of particular interest are those in which the replaceable chlorine atoms are on carbon atoms attached to oxygen, sulfur or nitrogen by a single-bond as in ethers, thioethers and imides because of the excellent insecticidal properties of the products. Preferred organic chloro compounds are the chlorodioxanes and particularly the dichloro-p-dioxanes such as 2,3-dichloro-p-dioxane and 2,5-dichloro-p-dioxane; tetrachloro-p-dioxane; alpha-chloro-m-dioxane; the chlorodithianes such as 2,3-dichloro-p-dithiane; the chlorothioxanes such as 2,3-dichloro-p-thioxane; 4,5-dichloro-m-dioxolane; and the N(1-chloro-2-haloethyl) phthalimides, and particularly N(1,2-chloroethyl) phthalimide.

As stated, the process of this invention is carried out in the presence of a catalytic amount of a metal chloride catalyst. The catalysts which are used in the present process accelerate rather than initiate the reaction and are chlorides of zinc, iron and tin. Zinc and tin chlorides are preferred because they give the lightest colored products. While the catalysts are referred to as chlorides, it is to be understood that metals or salts which under the reaction conditions are converted into the metal chlorides may be used as equivalents because of the nature of the reaction, and it is not intended that the process should be limited to one in which the metal chloride is added as such to the reaction mixture. The amount of catalyst used in the process of the present invention is not critical. A catalytic amount will generally be in the range of about 0.05 to 2 mole percent based on the dithiophosphoric acid reactant, with about 0.5 to about 1.0 mole percent being preferred.

The reaction temperature is any temperature in the range of about 40° to about 200° C. at which reaction takes place but below the decomposition temperature of the product or any intermediate produced in the process. The particular temperature used will thus depend on the reactants used. Some intermediates such as the monochlorodioxanethiol S-O,O-dialkyl phosphorodithioate produced from dichloro-p-dioxane and O,O-dialkyl dithiophosphoric acid, for instance, are unstable at temperatures above about 110° C. and require temperatures lower than might otherwise be required. Likewise, some products are unstable at elevated temperatures, and for this reason call for a preferred upper temperature limit of about 110° C. Generally, a temperature range between about 50° C. and about 105° C. and more preferably from about 70° to 95° C. for 1 to 6 hours will be sufficient to optimize yield and product purity.

The reaction is preferably carried out in a solvent which is inert in the reaction, although solvents are not necessary. When a solvent is used, aromatic volatile hydrocarbons such as benzene, toluene, xylenes, chlorobenzene, or cymene, cycloaliphatic volatile hydrocarbon such as cyclopentane or cyclohexane or carbon tetrachloride are preferred because they have the desired dissolving power for the reaction mixture without high dissolving power for the hydrogen chloride produced and are readily removed after the reaction is complete by distillation. Although water is generally considered deleterious to substitution reactions of this type, small amounts of water do not need to be excluded and the use of anhydrous catalysts is not necessary in the practice of this invention.

The improved process described by this invention is carried out in the presence of from 0.1 to 1.5 moles, preferably 0.1 to 0.6 mole, per mole of organic chloride, of an anhydride of an aliphatic carboxylic acid containing 2 to 5 carbon atoms. Typical anhydrides which can be used include acetic anhydride, propionic anhydride and butyric anhydride, acetic anhydride being preferred.

Recovery of the dithiophosphoric acid ester products produced in accordance with the improved process of this invention is conventional and does not require special techniques. Usually the organic phase is washed first with brine and then with water containing sufficient alkali to produce water-soluble salts of excess reactants, and solvent, if present, is removed by distillation or evaporation. Further purification by selective solvent extraction or by adsorptive agents is not usually necessary and the product is a highly satisfactory insecticide without subsequent treatments.

The products of this invention can be used as the sole toxic agent in insecticidal formulations or, if desired, in admixture with other toxicants for modification of the properties of the individual toxicants.

What I claim and desire to protect by Letters Patent is:

1. In the process of producing O,O-dialkyl dithiophosphoric acid esters by the reaction of an O,O-dialkyl dithiphosphoric acid with an organic chloride which contains at least one acid-replaceable chlorine atom on a carbon atom attached to oxygen, sulfur or nitrogen by a single bond in the presence of a catalytic amount of zinc chloride, ferrous chloride or stannous chloride, the improvement which comprises effecting said reaction in the presence of from 0.1 to 1.5 moles per mole of the organic chloride of an anhydride of a fatty acid containing 2 to 5 carbon atoms.

2. The process of claim 1 wherein the reaction is carried out in an inert solvent.

3. The process of claim 2 in which the anhydride is acetic anhydride.

4. The process of claim 3 in which the organic chloride is a chlorodioxane.

5. The process of claim 4 in which the chlorodioxane is a dichloro-p-dioxane.

6. The process of claim 5 in which the dichloro-p-dioxane is 2,3-dichloro-p-dioxane.

7. The process of claim 3 in which the organic chloride is N(1,2-dichloroethyl)phthalimide.

* * * * *